(12) United States Patent
Cox et al.

(10) Patent No.: US 6,652,579 B1
(45) Date of Patent: Nov. 25, 2003

(54) RADIOPAQUE STENT

(75) Inventors: Daniel L. Cox, Palo Alto, CA (US); Timothy A. Limon, Cupertino, CA (US); Wouter E. Roorda, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 187 days.

(21) Appl. No.: 09/603,762

(22) Filed: Jun. 22, 2000

(51) Int. Cl.$^7$ .................................................. A61F 2/06
(52) U.S. Cl. ...................... 623/1.34; 623/1.15; 623/1.16
(58) Field of Search ................................ 623/1.1, 1.15, 623/1.16, 1.34, 1.18

(56) References Cited

U.S. PATENT DOCUMENTS

| | | |
|---|---|---|
| 3,105,492 A | 10/1963 | Jeckel |
| 3,288,728 A | 11/1966 | Gorham |
| 3,657,744 A | 4/1972 | Ersek |
| 3,839,743 A | 10/1974 | Schwartz |
| 3,868,956 A | 3/1975 | Alfidi et al. |
| 3,993,078 A | 11/1976 | Bergentz et al. |
| 4,086,916 A | 5/1978 | Freeman et al. |
| 4,130,904 A | 12/1978 | Whalen |
| 4,140,126 A | 2/1979 | Choudhury |
| 4,159,719 A | 7/1979 | Haerr |
| 4,241,146 A | 12/1980 | Sivachenko et al. |
| 4,323,071 A | 4/1982 | Simpson et al. |
| 4,332,254 A | 6/1982 | Lundquist |
| 4,346,028 A | 8/1982 | Griffith |
| 4,387,952 A | 6/1983 | Slusher |
| 4,439,185 A | 3/1984 | Lundquist |
| 4,468,224 A | 8/1984 | Enzmann et al. |
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,531,933 A | 7/1985 | Norton et al. |
| 4,538,622 A | 9/1985 | Samson et al. |
| 4,553,545 A | 11/1985 | Maass et al. |
| 4,554,929 A | 11/1985 | Samson et al. |
| 4,560,374 A | 12/1985 | Hammerslag |
| 4,569,347 A | 2/1986 | Frisbie |

(List continued on next page.)

FOREIGN PATENT DOCUMENTS

| | | |
|---|---|---|
| DE | 36 40 745 A1 | 6/1987 |
| DE | 44 07 079 A1 | 9/1994 |
| DE | 296 07 916 U1 | 8/1996 |
| DE | 195 37 872 A1 | 4/1997 |
| EP | 0 045 627 A1 | 10/1982 |
| EP | 0 062 300 A2 | 10/1982 |

(List continued on next page.)

OTHER PUBLICATIONS

Application for U.S. Letter Patent ser. No. 08/233,046, filed Apr. 25, 1994.
Application for U.S. Letter Patent ser. No. 08/559,931, filed Nov. 17, 1995.
Application for U.S. Letter Patent ser. No. 08/564,936 (FWC of 08/233,046) filed Nov. 30, 1995.

(List continued on next page.)

Primary Examiner—David H. Willse
Assistant Examiner—Javier G Blanco
(74) Attorney, Agent, or Firm—Fulwider Patton Lee & Utecht, LLP

(57) ABSTRACT

A tubular stent formed from a plurality of cylindrical rings and connecting links where selected connecting links are of comparatively high mass in relation to the other links. The high-mass links have sufficient mass to be visible during a fluoroscopy procedure when formed from a moderately radiopaque material such as stainless steel. The high-mass links being arranged in a spiral pattern along the length of the stent to ensure that the stent is fluoroscopically visible regardless of the stents orientation during the implantation procedure.

35 Claims, 8 Drawing Sheets

U.S. PATENT DOCUMENTS

| | | |
|---|---|---|
| 4,571,240 A | 2/1986 | Samson et al. |
| 4,572,186 A | 2/1986 | Gould et al. |
| 4,580,568 A | 4/1986 | Gianturco |
| 4,616,652 A | 10/1986 | Simpson |
| 4,619,246 A | 10/1986 | Molgaard-Nielsen et al. |
| 4,633,873 A | 1/1987 | Dumican et al. |
| 4,649,922 A | 3/1987 | Wiktor |
| 4,650,466 A | 3/1987 | Luther |
| 4,655,771 A | 4/1987 | Wallsten |
| 4,656,083 A | 4/1987 | Hoffman et al. |
| 4,665,918 A | 5/1987 | Garza et al. |
| 4,681,110 A | 7/1987 | Wiktor |
| 4,699,611 A | 10/1987 | Bowden |
| 4,706,671 A | 11/1987 | Weinrib |
| 4,718,907 A | 1/1988 | Karwoski et al. |
| 4,722,335 A | 2/1988 | Vilasi |
| 4,723,549 A | 2/1988 | Wholey et al. |
| 4,725,334 A | 2/1988 | Brimm |
| 4,728,328 A | 3/1988 | Hughes et al. |
| 4,732,152 A | 3/1988 | Wallsten et al. |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,748,986 A | 6/1988 | Morrison et al. |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,771,777 A | 9/1988 | Horzewski et al. |
| 4,776,337 A | 10/1988 | Palmaz |
| 4,790,315 A | 12/1988 | Mueller, Jr. et al. |
| 4,795,458 A | 1/1989 | Regan |
| 4,800,882 A | 1/1989 | Gianturco |
| 4,816,339 A | 3/1989 | Tu et al. |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,323,071 A | 5/1990 | Simpson et al. |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,990,155 A | 2/1991 | Wilkoff |
| 4,994,071 A | 2/1991 | MacGregor |
| 4,994,298 A | 2/1991 | Yasuda |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,047,050 A | 9/1991 | Arpesani |
| 5,053,048 A | 10/1991 | Pinchuk |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,067,491 A | 11/1991 | Taylor, II et al. |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,085,629 A | 2/1992 | Goldberg et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,108,755 A | 4/1992 | Daniels et al. |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,156,619 A | 10/1992 | Ehrenfeld |
| 5,156,623 A | 10/1992 | Hakamatsuka et al. |
| 5,158,548 A | 10/1992 | Lau et al. |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,977 A | 3/1993 | Hoffman, Jr. et al. |
| 5,197,978 A | 3/1993 | Hess |
| 5,222,971 A | 6/1993 | Willard et al. |
| 5,226,913 A | 7/1993 | Pinchuk |
| 5,234,456 A | 8/1993 | Silvestrini |
| 5,234,457 A | 8/1993 | Andersen |
| 5,236,446 A | 8/1993 | Dumon |
| 5,236,447 A | 8/1993 | Kubo et al. |
| 5,242,452 A | 9/1993 | Inoue |
| 5,269,802 A | 12/1993 | Garber |
| 5,282,823 A | 2/1994 | Schwartz et al. |
| 5,282,824 A | 2/1994 | Gianturco |
| 5,282,860 A | 2/1994 | Matsuno et al. |
| 5,289,831 A | 3/1994 | Bosley |
| 5,290,271 A | 3/1994 | Jernberg |
| 5,290,305 A | 3/1994 | Inoue |
| 5,292,331 A | 3/1994 | Boneau |
| 5,304,200 A | 4/1994 | Spaulding |
| 5,306,286 A | 4/1994 | Stack et al. |
| 5,314,444 A | 5/1994 | Gianturco |
| 5,314,472 A | 5/1994 | Fontaine |
| 5,330,500 A | 7/1994 | Song |

| | | |
|---|---|---|
| 5,342,348 A | 8/1994 | Kaplan |
| 5,342,621 A | 8/1994 | Eury |
| 5,344,425 A | 9/1994 | Sawyer |
| 5,354,308 A | 10/1994 | Simon et al. |
| 5,356,433 A | 10/1994 | Rowland et al. |
| 5,360,443 A | 11/1994 | Barone et al. |
| 5,364,354 A | 11/1994 | Walker et al. |
| 5,366,504 A | 11/1994 | Andersen et al. |
| 5,383,892 A | 1/1995 | Cardon et al. |
| 5,383,927 A | 1/1995 | De Goicoechea et al. |
| 5,389,106 A | 2/1995 | Tower |
| 5,395,390 A | 3/1995 | Simon et al. |
| 5,413,597 A | 5/1995 | Krajicek |
| 5,421,955 A | 6/1995 | Lau et al. |
| 5,423,849 A | 6/1995 | Engelson et al. |
| 5,449,373 A | 9/1995 | Pinchasik et al. |
| 5,476,506 A | 12/1995 | Lunn |
| 5,514,154 A | 5/1996 | Lau et al. |
| 5,527,324 A | 6/1996 | Krantz et al. |
| 5,562,728 A | 10/1996 | Lazarus et al. |
| 5,569,295 A | 10/1996 | Lam |
| 5,599,301 A | 2/1997 | Jacobs et al. |
| 5,601,593 A | 2/1997 | Freitag |
| 5,609,629 A | 3/1997 | Fearnot et al. |
| 5,617,878 A | 4/1997 | Taheri |
| 5,628,787 A | 5/1997 | Mayer |
| 5,630,829 A | 5/1997 | Lauterjung |
| 5,636,641 A | 6/1997 | Fariabi |
| 5,637,113 A | 6/1997 | Tartaglia et al. |
| 5,649,951 A | 7/1997 | Davidson |
| 5,653,691 A | 8/1997 | Rupp et al. |
| 5,674,242 A | 10/1997 | Phan et al. |
| 5,421,955 A | 1/1998 | Lau et al. |
| 5,707,388 A | 1/1998 | Lauterjung |
| 5,716,393 A | 2/1998 | Lindenberg et al. |
| 5,725,572 A * | 3/1998 | Lam et al. ............... 623/1 |
| 5,741,327 A | 4/1998 | Frantzen |
| 5,755,781 A | 5/1998 | Jayaraman |
| 5,759,192 A | 6/1998 | Saunders |
| 5,776,161 A | 7/1998 | Globerman |
| 5,800,526 A | 9/1998 | Anderson et al. |
| 5,810,868 A | 9/1998 | Lashinski et al. |
| 5,827,321 A | 10/1998 | Roubin et al. |
| 5,836,966 A | 11/1998 | St. Germain |
| 5,843,120 A | 12/1998 | Israel et al. |
| 5,855,600 A | 1/1999 | Alt |
| 5,858,556 A | 1/1999 | Eckert et al. |
| 5,868,781 A | 2/1999 | Killion |
| 5,868,783 A | 2/1999 | Tower |
| 5,907,893 A | 6/1999 | Zadno-Azizi et al. |
| 5,913,895 A | 6/1999 | Burpee et al. |
| 5,919,126 A | 7/1999 | Armini |
| 5,922,020 A | 7/1999 | Klein et al. |
| 5,922,021 A | 7/1999 | Jang |
| 5,928,280 A | 7/1999 | Hansen et al. |
| 5,931,867 A | 8/1999 | Haindl |
| 5,935,162 A | 8/1999 | Dang |
| 5,938,697 A | 8/1999 | Killion et al. |
| 5,964,798 A * | 10/1999 | Imran ............... 623/1 |
| 5,968,069 A | 10/1999 | Dusbabek et al. |
| 5,976,169 A | 11/1999 | Imran |
| 6,017,365 A | 1/2000 | Von Oepen |
| 6,022,374 A | 2/2000 | Imran |
| 6,027,526 A | 2/2000 | Limon et al. |
| 6,033,435 A | 3/2000 | Penn et al. |
| 6,042,597 A | 3/2000 | Kveen et al. |
| 6,042,606 A | 3/2000 | Frantzen |
| 6,066,168 A | 5/2000 | Lau et al. |
| 6,090,127 A | 7/2000 | Globerman |
| 6,099,561 A | 8/2000 | Alt |
| 6,113,628 A | 9/2000 | Borghi |
| 6,312,459 B1 * | 11/2001 | Huang et al. ............... 623/1.15 |
| 6,315,794 B1 | 11/2001 | Richter |
| 6,540,774 B1 * | 4/2003 | Cox ............... 623/1.15 |
| 2003/0069630 A1 * | 4/2003 | Burgermeister et al. ... 623/1.15 |

FOREIGN PATENT DOCUMENTS

| | | |
|---|---|---|
| EP | 0 201 466 A2 | 11/1986 |
| EP | 0 221 570 A2 | 5/1987 |
| EP | 0 338 816 A2 | 10/1989 |
| EP | 0 357 003 A2 | 3/1990 |
| EP | 0 361 192 A3 | 4/1990 |
| EP | 0 364 787 A1 | 4/1990 |
| EP | 0 372 789 A3 | 6/1990 |
| EP | 0 380 668 B1 | 8/1990 |
| EP | 0 407 951 A2 | 1/1991 |
| EP | 0 423 916 A1 | 4/1991 |
| EP | 0 488 016 A1 | 9/1991 |
| EP | 0 421 729 A2 | 10/1991 |
| EP | 0 335 341 B1 | 4/1992 |
| EP | 0 517 075 A1 | 9/1992 |
| EP | 0 517 075 B1 | 9/1992 |
| EP | 0 540 290 A2 | 5/1993 |
| EP | 0 541 443 A1 | 5/1993 |
| EP | 0 565 251 A1 | 10/1993 |
| EP | 0 578 998 B1 | 1/1994 |
| EP | 0 604 022 A1 | 6/1994 |
| EP | 0 606 165 A1 | 7/1994 |
| EP | 0 621 017 A1 | 10/1994 |
| EP | 0 679 372 A2 | 11/1995 |
| EP | 0 679 373 A2 | 11/1995 |
| EP | 0 688 545 A1 | 12/1995 |
| EP | 0 709 068 A2 | 5/1996 |
| EP | 0 712 614 A1 | 5/1996 |
| EP | 0 800 801 A1 | 10/1996 |
| EP | 0 380 668 B1 | 12/1996 |
| EP | 0 758 541 A1 | 2/1997 |
| EP | 0 806 190 A1 | 11/1997 |
| EP | 0 540 290 B1 | 1/1998 |
| EP | 0 847 733 A1 | 6/1998 |
| EP | 0 864 302 A2 | 9/1998 |
| FR | 2 677 872 | 12/1992 |
| GB | 2 070 490 A | 9/1981 |
| GB | 2 135 585 A | 11/1983 |
| JP | 57-89859 | 6/1982 |
| JP | SHO 58-501458 | 9/1983 |
| JP | 62-231657 | 10/1987 |
| JP | 62-235495 | 10/1987 |
| JP | SHO 63-214264 | 9/1988 |
| JP | 01083685 A | 3/1989 |
| JP | 64-83685 | 3/1989 |
| JP | HEI 02-174859 | 7/1990 |
| JP | HEI 02-255157 | 10/1990 |
| JP | 3-9745 | 1/1991 |
| JP | 030009746 A | 1/1991 |
| JP | 3-151983 | 6/1991 |
| JP | HEI 04-25755 | 2/1992 |
| JP | 6-181993 | 7/1994 |
| JP | 8-336597 | 12/1996 |
| JP | 9-56824 | 3/1997 |
| JP | 10201856 A | 4/1998 |
| JP | 11-19219 | 1/1999 |
| WO | WO 89/01798 | 3/1989 |
| WO | WO 89/08433 | 9/1989 |
| WO | WO 91/07139 | 5/1991 |
| WO | WO 91/17789 | 11/1991 |
| WO | WO 92/06734 | 4/1992 |
| WO | WO 92/09246 | 6/1992 |
| WO | WO 93/06792 | 4/1993 |
| WO | WO 94/17754 | 8/1994 |
| WO | WO 95/03010 | 2/1995 |
| WO | WO 95/23563 | 9/1995 |

| WO | WO 95/26695 | 10/1995 | |
| --- | --- | --- | --- |
| WO | WO 95/29647 | 11/1995 | |
| WO | WO 96/09013 | 3/1996 | |
| WO | WO 96/24393 | 8/1996 | |
| WO | WO 96/26689 | 9/1996 | |
| WO | WO 97/25937 | 7/1997 | |
| WO | WO 97/45073 | * 12/1997 | ............ A61F/2/06 |
| WO | WO 98/20927 | 5/1998 | |
| WO | WO 98/22159 | 5/1998 | |
| WO | WO 98/32412 | 7/1998 | |
| WO | WO 98/48734 | 11/1998 | |
| WO | WO 98/58600 | 12/1998 | |
| WO | WO 99/02105 | 1/1999 | |
| WO | WO 99/15107 | 4/1999 | |
| WO | WO 99/17680 | 4/1999 | |
| WO | WO 99/39661 | 8/1999 | |

OTHER PUBLICATIONS

Application for U.S. Letter Patent ser. No. 09/298,263, filed Apr. 22, 1999.

Union Carbide A-174 Silane, Sales Brochure, Union Carbide Adhesion Promoters, Jan. 1968 (5 pages).

Dotter, Charles T., Transluminally Placed Coilspring Endarterial Tube Grafts, *Investigative Radiology*, pp. 329–332, vol. 1, No. 5, Sep./Oct. 1969.

Rösch, J., M.D., et al., Transjugular Intrahepatic Portacaval Shunt: An Experimental Work, *The American Journal of Surgery*, pp. 588–592, vol. 121, May 1971.

Union Carbide Technology Letter, New business Department—Parylene, Oct. 1973, No. 7 (8 pages).

Union Carbide, Electronic Materials, Parylene Products, Oct. 1973, No. 9 (23 pages).

Union Carbide Technology, May 1974, No. 11 (12 pages).

Union Carbide Technology Letter, Oct. 1975, No. 15 (13 pages).

Union Carbide, Electronic Materials, Parylene Products, Mar. 1976, No. 16 (4 pages).

Eskin, S.G., et al., Growth of Cultured Calf Aortic Smooth Muscle Cells on Cardiovascular Prosthetic Materials, J. Biomed. Mater. Res., vol. 10, pp. 113–122 (1976).

Loeb, Gerald E., et al., Parylene as a Chronically Stable, Reproducible Microelectrode Insulator, IEEE Transactions on Biomedical Engineering, Mar. 1977 (pp. 121–128).

Union Carbide, Electronic Materials, Parylene Products, Aug. 1977, No. 18, (7 pages).

Union Carbide, Electronic Materials, Parylene Products, Oct. 1977, No. 1 Revision 2 (7 pages).

Union Carbide, Electronic Materials, Parylene Products, Oct. 1977, No. 2 Revision (9 pages).

Union Carbide, Electronic Materials, Parylene Products, Oct. 1977, No. 3 (21 pages).

Union Carbide, Electronic Materials, Parylene Products, Oct. 1977, No. 4 (13 pages).

Union Carbide, Electronic Materials, Parylene Products, Oct. 1977, No. 6 (12 pages).

Union Carbide, Electronic Materials, Parylene Products, Oct. 1977, No. 7 Revision 1 (8 pages).

Union Carbide, Electronic Materials, Parylene Products, Oct. 1977, No. 8 (19 pages).

Union Carbide, Electronic Materials, Parylene Products, Oct. 1977, No. 10 (50 pages).

Union Carbide, Electronic Materials, Parylene Products, Oct. 1977, No. 11 (12 pages).

Union Carbide, Electronic Materials, Parylene Products, Oct. 1977, No. 12 Revision 1 (6 pages).

Union Carbide, Electronic Materials, Parylene Products, Oct. 1977, No. 13 Revision 1 (7 pages).

Union Carbide, Electronic Materials, Parylene Products, Oct. 1977, No. 14 Revision 1 (11 pages).

Union Carbide, Electronic Materials, Parylene Products, Oct. 1977, No. 15 Revision 1 (8 pages).

Union Carbide, Electronic Materials, Parylene Products, Oct. 1977, No. 17 Revision 1 (11 pages).

ISEE Transactions on Biomedical Engineering, vol. BME–27, No. 11, Nov. 1980 (5 pages).

Sadhir, R.K., et al., The Adhesion of Glow–Discharge Polymers, Silastic and Parylene to Implantable Platinum Electrodes: Results of Tensire Pull Tests After Exposure to Isotonic Sodium Chloride, *Biomaterials*, pp. 239–243, vol. 2, Oct. 1981.

Hah, Allen W., et al., Glow Discharge Polymers as Coatings for Implanted Devices, ISA, pp. 109–113, 1981.

Union Carbide, Electrode Materials, Parylene Products, Jan. 18, 1982 No. 5 Revision 4 (17 pages).

Dotter, Charles t., et al., Transluminal Expandable Nitinol Coil Stent Grafting: Preliminary Report, *Radiology Journal*, pp. 259–260, Apr. 1983.

Cragg, Andrew, M.D., Non–Surgical Placement of Arterial Endoprostheses: A New Technique Using Nitinol Wire, *Radiology*, pp. 261–263, Apr. 1983.

Hahn, Allen W., et al., Biocompatibility of Glow–discharge–Polymerized Films and Vacuum–Deposited Parylene, *Journal of Applied Polymer Science: Applied Polymer Symposium 38*, pp. 55–64 (1984).

Maass, et al., Radiology Follow–Up of Transluminally Inserted Vascular Endoprostheses: An Experimental Study Using Expanding Spirals, *Radiology Journal*, pp. 659–663, 1984.

70th Scientific Assembly and Annual Meeting, *Radiology*, Washington, D.C., Nov. 25–30, 1984, vol. 153(P).

Casper, R.A., et al., Fiber–Reinforced Absorbable Composite for Orthopedic Surgery, *Polymeric Materials Science and Engineering*, Proceedings of ACS Division of Polymeric Materials, vol. 53, Fall Meeting, 1985.

Wright, Kenneth C., et al., Percutaneous Endovascular Stents: An Experimental Evaluation, *Radiology Journal*, pp. 73–77, vol. 156, No. 1, Jul. 1985.

Palmaz, Julio C., et al., Expandable Intraluminal Graft: A Preliminary Study, *Radiology Journal*, pp. 73–77, vol. 156, No. 1, Jul. 1985.

C.R. Bard, PE Plus Peripheral Balloon dilatation Catheter, Aug. 1985.

Program, Dy 2 (Nov. 18) The Radiological Society of North America, *Radiology*,1985.

Charnsangavej, Chusilp, M.D., et al., Endovascular Stent for Use in aortic Dissection: An In Vitro Experiment, *Radiology*, pp. 323–324, vol. 157, No. 2, Nov. 1985.

Wallace, Michael J., et al., Tracheobronchial Tree: Expandable Metallic Stents Used in Experimental and Clinical Applications (Work in Progress), *Radiology*, pp. 309–312, vol. 158, Feb. 1986.

Charnsangavej, Chusilp, M.D., et al., Stenosis of the Vena Cava: Preliminary Assessment of Treatment with Expandable Metallic Stents, *Radiology*, pp. 295–298, vol. 161, No. 2, Nov. 1986.

72nd Scientific Assembly and Annual Meeting: RSNA Scientific Program, *Radiology*, Chicago, Nov. 30–Dec. 5, 1986, vol. 161(P).

Duprat, Gerard., Jr., M.D., et al., Flexible Balloon–Expandable Stent for Small Vessels, *Radiology Journal*, pp. 276–278, vol. 162, No. 1, Jan. 1987.

Rösch, Josef, M.D., et al., Experimental Intrahepatic Portcaval Anastomosis: Use of Expandable Gianturco Stents, *Radiology*, pp. 481–485, vol. 162, No. 2, Feb. 1987.

Yuen, Ted G.H., et al., Tissue Response to Potential Neuroprosthetic Materials Implanted Subdurally, *Biomaterials*, pp. 67–82, vol. 8, Mar. 1987.

Rösch, Josef, M.D., et al., Gianturco Expandable Stents in Experimenal and Clinical Use, Twelfth Annual Course on "Diagnostic Angiography and Interventional Radiology" pp. 121–124, Mar. 23–26, 1987 (San Diego, California).

Lawrence, David D., Jr., et al., Percutaneous Endovascular Graft: Experimental Evaluation, *Radiology*, pp. 357–360, vol. 163, No. 2, May 1987.

Kelley, Benjamin S., et al., Totally Reformable High–Strength Composite Material, *Advances in Biomedical Polymers*, Edited by Charles G. Gebelein (1987).

Rösch, Josef, M.D., et al., Gianturco Expandable Wire Stents in the Treatment of Superior Vena Cava Syndrome Recurring After Maximum–Tolerance Radiation, *Cancer*, pp. 1243–1246, vol. 60, No. 6, Sep. 1987.

Nichols, M.F., et al., *Electrical Insulation of Implantable Devices by Composite Polymer Coatings*, ISA pp. 57–62, 1987.

Schmidt, E. M., et al., Long–Term Implants of Parylene–C Coated Microelectrodes, *Medical & Biological Engineering & Computing*, pp. 96–101, Jan. 1988.

Yoshioka, Tetsuya, et al., Self–Expanding Endovascular Graft: An Experimental Study in Dogs, *American Journal of Roentgeriology*, pp. 673–676, vol. 151, Oct. 1988.

Olson, Roger, Parylene, a Biostable Coating for Medical Applications, for Nova Tran Parylene Coating Services, Jul. 25, 1988/Nov. 14, 1988.

Yoshioka, Tetsuya, et al., Development and Clinical application of Biliary Endoprostheses Using Expandable Metallic Stents, *Japan Radiological Society*, pp. 1183–1185, vol. 48, No. 9, 1988 (with translation).

Rösch, Josef, M.D., et al., Modified Gianturco Expandable Wire Stents in Experimental and Clinical Use, *Annales de Radiologie*, pp. 100–103, vol. 31, No. 2, 1988.

Mirich, David, M.D., et al., Percutaneously Placed Endovascular Grafts for Aortic Aneurysms: Feasibility Study, *Radiology*, pp. 1033–1037, Mar. 1989 Part 2.

Beach, W.F., et al., Xylylene Polymers, *Encyclopedia of Polymer Science and Engineering*, vol. 17, 2d Ed. pp. 990–1025, 1989.

Muller, David W.M., et al., Advances in Coronary Angioplasty: Endovascular Stents, *Coronary artery Disease*, vol. 1, No. 4, Jul./Aug. 1990.

Loh, L.H., et al., Plasma Enhanced Parylene Deposition, *Antec*, pp. 1099–1103, 1991.

Wong, S.C., M.D., et al., An Update on Coronary Stents, *Cardio*, pp. 30–50, Feb. 1992.

The Parylene Press (A Publication of Specialty Coating Systems, Inc.) Winter 1992 (7 pages).

Charlson, E.M., et al., Temperature Selective Deposition of Parylene–C, *IEEE Transactions on Biomedical*, pp. 202–206, vol. 39, No. 2, Feb. 1992 Engineering.

Bull, Victor A., Parylene Coating For Medical Applications, *Medical Product Manufacturing News*, Mar. 1993.

The Parylene Press (A Publication of Specialty Coating Systems, Inc.) Spring 1993 (6 pages).

The Parylene Press (A Publication of Specialty Coating Systems, Inc.) Summer 1993(4 pages).

Information Regarding Parylene–C Coating for ACS Metal Stent, In–House Memorandum from Ed Newton to Joe Callol, et al., Oct. 15, 1993, attaching Parylene, A Biostable Coating for Medical Applications by Roger Olson.

Moody, JoAnne, Vacuum Coating Ultrasonic Transducers, *Sensors*, Dec. 1993 (1 page).

Gebelein, Charles G., et al., (Eds.) Biomedical and Dental Applications of Polymers *Polymer Science and Technology*, pp. 143–161, vol. 14 (Undated).

Typical Parylene Properties, Printout, Para Tech Coating Company; Lab Top® Parylene Deposition System Model 3000, Sales Brochure, Para Tech Coating Company (7 pages) (Undated).

Nova Tran™ Custon Coating Services, Parylene Conformal Coating, Brochure, Union Carbide (8 pages) (Undated).

Parylene Environmentally Compatible Conformal Coatings for Electronic Components Assemblies and Precision Parts, Brochure, Union Carbide Electronics Division (14 pages) (Undated).

Parylene and Nova Tran™ Parylene Coatings Services for Unmatched Conformal Coating Performance, Brochure, Union Carbide Specialty Coating Systems (21 pages) (Undated).

Repair and Recoating of Parylene Coated Printed Circuit Boards, Brochure, Union Carbide Specialty Coating Systems (15 pages) (Undated).

Parylene, A Biostable Coatings for Medical Applications, Brochure, Union Carbide Specialty Coating Systems (6 pages) (Undated).

* cited by examiner

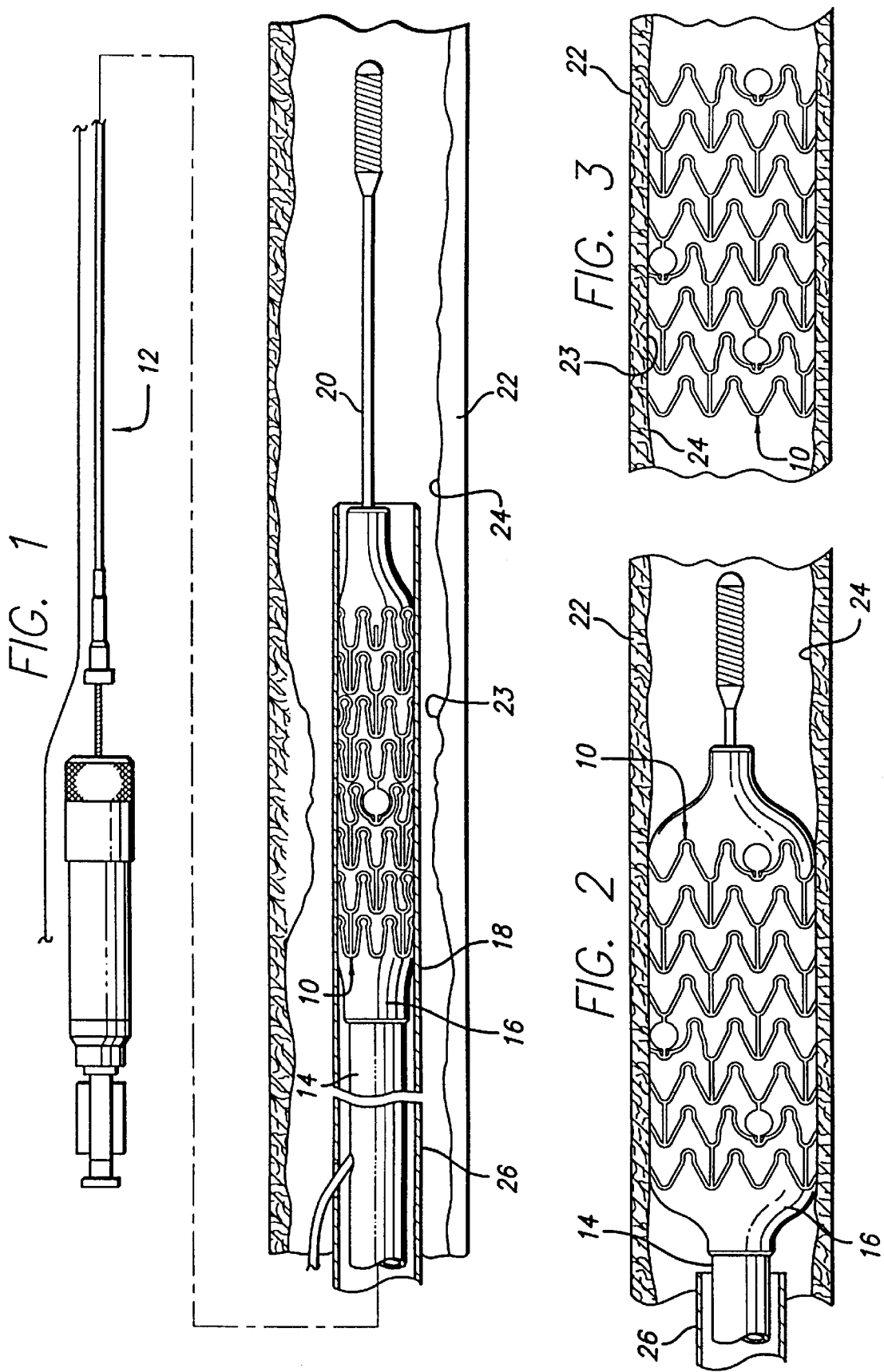

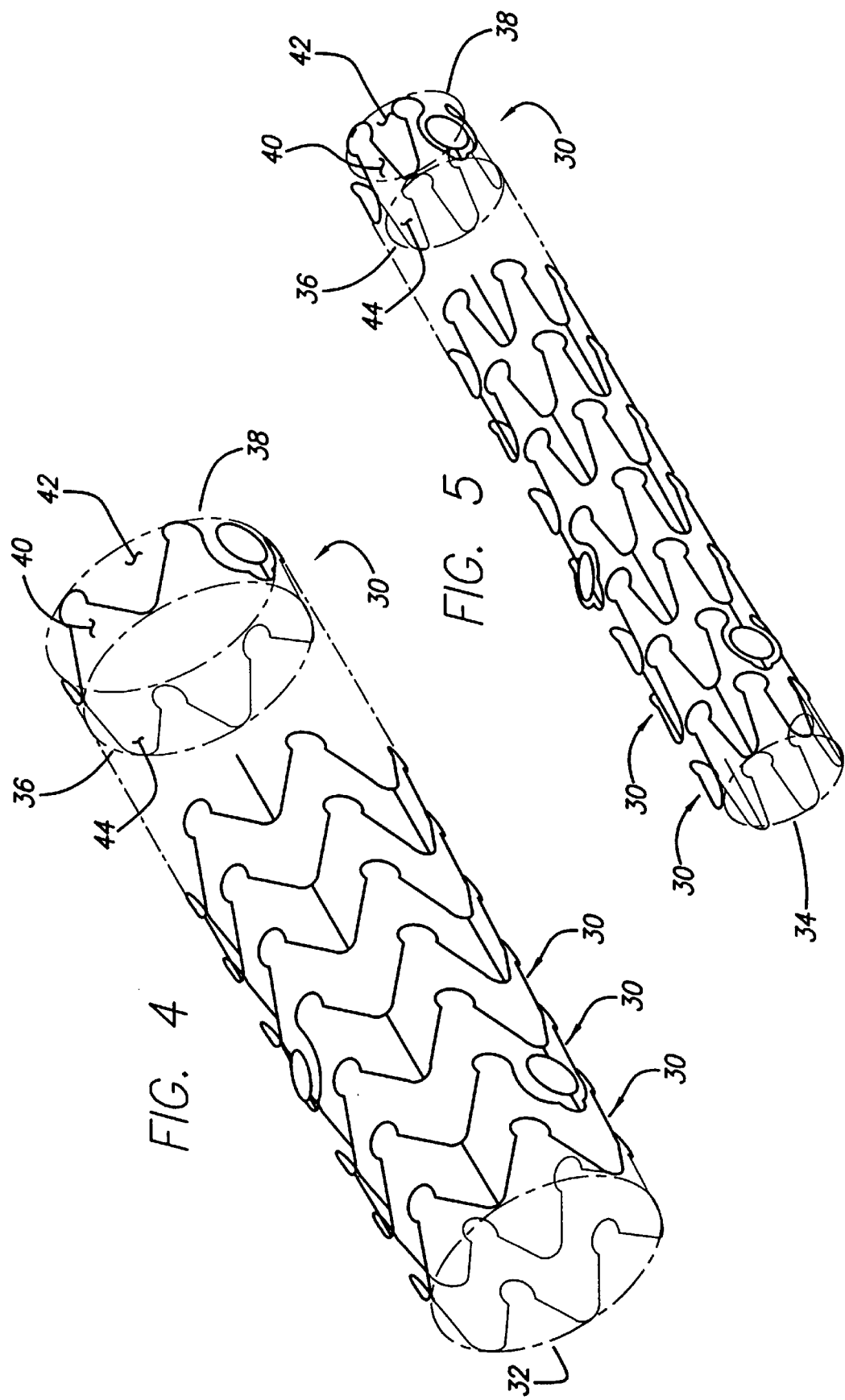

RADIOPAQUE STENT

BACKGROUND OF THE INVENTION

The present invention relates generally to endoprosthesis devices, which are commonly referred to as stents, and more particularly to radiopaque stents.

Stents are generally thin walled tubular-shaped devices composed of complex patterns of interconnecting struts which function to hold open a segment of a blood vessel or other body lumen such as a coronary artery. They also are suitable for supporting a dissected arterial lining or intimal flap that can occlude a vessel lumen. At present, there are numerous commercial stents being marketed throughout the world. These devices are typically implanted by use of a catheter which is inserted at an easily accessible location and then advanced through the vasculature to the deployment site. The stent is initially maintained in a radially compressed or collapsed state to enable it to be maneuvered through the lumen. Once in position, the stent is deployed. In the case of self-expanding stents, deployment is achieved by the removal of a restraint, such as the retraction of a delivery sheath. In the case of balloon expandable stents, deployment is achieved by inflation of a dilation balloon about which the stent is carried on a stent-delivery catheter.

The stent must be able to simultaneously satisfy a number of mechanical requirements. First and foremost, the stent must be capable of withstanding the structural loads, namely radial compressive forces, imposed on the stent as it supports the walls of a vessel lumen. In addition to having adequate radial strength or more accurately, hoop strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion which typically requires substantial deformation of localized portions of the stent's structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

In addition to meeting the mechanical requirements described above, it is preferable that a stent also be fluoroscopically visible. Fluoroscopy has typically been relied upon to facilitate the precise placement of a stent as well as to verify the position of a stent within a patient throughout its service life. The use of radiopaque materials in the construction of a stent allows for its direct visualization. The most common materials used to fabricate stents are stainless steel and nickel-titanium alloys. These materials are known to be bio-compatible and satisfy the mechanical requirements for stents. However, neither of the materials is particularly radiopaque. This factor, in combination with the minimal surface area and thin wall thickness of typical stent patterns, renders stents produced from these materials insufficiently radiopaque to be adequately visualized with fluoroscopy procedures. Alternative structural materials are either excessively radiopaque or have not been proven to be sufficiently biocompatible for long term use in a vascular setting. For these reasons, simply constructing a radiopaque stent wholly out of a single material has heretofore not been considered a viable option. Thus, the art has moved in the direction of combining different materials to produce a mechanically sound, biocompatible and fluoroscopically visible stent. A number of such approaches have been developed.

One means frequently described for accomplishing flouroscopic visibility is the physical attachment of radiopaque markers to the stent. Conventional radiopaque markers, however, have a number of limitations. Upon attachment to a stent, such markers may project from the surface of the stent, thereby comprising a departure from the ideal profile of the stent. Depending on their specific location, the marker may either project inwardly to disrupt blood flow or outwardly to traumatize the walls of the blood vessel. Additionally, galvanic corrosion may result from the contact of two disparate metals, i.e., the metal used in the construction of the stent and the radiopaque metal of the marker. Such corrosion could eventually cause the marker to become separated from the stent which may be problematic should the marker be swept downstream. Finally, although such markers are typically fairly small, this approach does cause the radiopaque material to come into direct contact with living tissue which may be problematic should there be any biocompatibility issues.

Stents also have been previously marked by plating selected portions thereof with radiopaque material. However, a number of disadvantages are associated with this approach as well. This again causes the radiopaque material to come into direct contact with living tissue which, depending on the total area that is plated, can amount to a sizeable exposure. Additionally, when the stent is expanded certain portions undergo substantial deformation, creating a risk that cracks may form in the plating causing portions of the plating to separate from the underlying substrate. This has the potential for creating jagged edges that may inflict physical trauma on the lumen wall tissue or cause turbulence in the blood flowing past the stent, thereby inducing thrombogenesis. Moreover, once the underlying structural material becomes exposed, interfaces between the two disparate metals become subject to galvanic corrosion. Further, should the plating pattern cover less than all of the stent's surfaces, the margins between the plated and unplated regions are also subject to galvanic corrosion.

As a further alternative, a stent structure has been described that is formed from a sandwich of structural and radiopaque materials. Three tubes of the materials are codrawn and heat treated to create a structural/radiopaque/structural composite. Struts and spines are then formed in the tube by cutting an appropriate pattern of voids into the tube as is well known in the art. While this approach does provide a stent that is radiopaque and that fulfills the necessary mechanical requirements, the thin cross section of the radiopaque material is nonetheless exposed along the edges of all cut lines. The biocompatiblity of the radiopaque material therefore remains an issue and more significantly, a sizeable area is thereby created that is subject to galvanic corrosion. Any cuts in the sandwich structure cause two disparate metal interfaces, i.e., the juncture between the outer structural layer and the central radiopaque layer as well the juncture between the central radiopaque layer and the inner structural layer, to become exposed to blood, an electrolytic solution.

As can be seen, composite stents, whether of the plated or coated type, sandwich type, or simply those equipped with markers, have several disadvantages; namely, potential flaking of the radiopaque coating or plating, galvanic corrosion, or poor biocompatibililty. Thus, a stent configuration is required that overcomes the shortcomings inherent in previously known devices. Preferably, such a stent would be biocompatible, possess the required mechanical characteristics, would be sufficiently radiopaque to be readily visible using fluoroscopy procedures, and would be formed from a single material.

SUMMARY OF THE INVENTION

The present invention provides a stent made from a single material that overcomes the shortcomings of previously known stent devices. The stent fulfills all of the mechanical and structural requirements attendant to its function as a stent. Moreover, in contrast to the prior art, at least a portion of the stent is fluoroscopically visible without the addition of an extra layer of radiopaque material.

The stent of the present invention includes generally a plurality of cylindrical rings that are interconnected by a plurality of links. The stent's advantages are achieved by incorporating high metal mass density into portions of the stent such as into selected connecting links which possess sufficient mass to be readily visible using typical fluoroscopy procedures. In order to avoid the difficulties associated with machining differential wall thickness stents, in an exemplary embodiment, the stent has a uniform wall thickness and the selected high-mass links are formed as circular disks or as other shapes with a comparatively large surface area with respect to the narrow rectangular surfaces of the standard connecting links and cylindrical rings which form the body of the stent.

Each of the cylindrical rings making up the stent have a proximal end and a distal end and a cylindrical plane defined by a cylindrical outer wall surface that extends circumferentially between the proximal end and the distal end of the cylindrical ring. The cylindrical rings are interconnected by at least one standard or high-mass connecting link which attaches one cylindrical ring to an adjacent cylindrical ring. Generally, at least every other ring will include at least one high-mass link. In addition, each high-mass link is circumferentially offset from the previous high-mass link in a preceding ring to establish a spiral pattern of high-mass links around the periphery of the stent. The spiral pattern of high-mass links renders the stent fluoroscopically visible regardless of the stent's orientation within a body lumen.

The cylindrical rings typically comprise a plurality of alternating peaks and valleys, where the valleys of one cylindrical ring are circumferentially offset from the valleys of an adjacent cylindrical ring. In this configuration, the connecting links attach each cylindrical ring to an adjacent cylindrical ring so that the links are positioned substantially within one of the valleys and attach the valley to an adjacent peak.

While the cylindrical rings and connecting links generally are not separate structures, they have been conveniently referred to as rings and links for ease of identification. Further, the cylindrical rings can be thought of as comprising a series of U's, W's and Y-shaped structures in a repeating pattern. Again, while the cylindrical rings are not divided up or segmented into U's, W's and Y's, the pattern formed by the rings resembles such a configuration. The U's, W's and Y's promote flexibility in the stent primarily by flexing and by tipping radially outwardly as the stent is delivered through a tortuous vessel.

The connecting links are positioned so that they are within the curved part of a U-shaped portion. Where the connecting link is a high-mass link, the U-shaped portion broadens to form a generally semicircular shape. Positioning the connecting links within a U-shaped portion generally increases the amount of vessel wall coverage, and where a high-mass link is used, vessel wall coverage is further increased locally due to the large surface area of the high-mass link. Since the connecting links do not substantially deform (if at all) when the stent is expanded, the selected use of high-mass links does not increase the balloon pressure required to expand a balloon expandable embodiment of the stent, nor do the high mass links increase the spring tension required to expand a self-expanding embodiment of the stent.

The number and location of high-mass connecting links can be varied as the application requires. Since the high-mass links typically have the same thickness as the standard connecting links, substituting standard links with high-mass links has very little impact on the overall longitudinal flexibility of the stent. Thus, in typical stent positioning applications the stent may have only one high-mass link between every other cylindrical ring. In applications, where a high degree of radiopacity is desired, the stent may have multiple high-mass links between each adjacent cylindrical ring.

In one embodiment of the invention, selected portions of the rings and links are of a higher metal mass density than the remaining portions of the stent. So for example, a portion of the stent that would have a spiral shape if traced around the circumference of the stent would have a higher metal mass density than the remaining portions of the stent. When the stent is oriented in a vessel, the higher mass will be readily visible under fluoroscopy. Also, since the higher mass material is in a spiral shape, it will be much easier to determine the position of the stent with respect to the vessel and to more easily determine whether the stent is fully expanded and implanted in the vessel.

The stent may be formed from a tube by laser cutting the pattern of cylindrical rings and connecting links in the tube. The stent also may be formed by laser cutting a flat metal sheet in the form of the cylindrical rings and links, and then rolling the pattern into the shape of the tubular stent and providing a longitudinal weld to form the stent.

These and other features and advantages of the present invention will become apparent from the following detailed description, which when taken in conjunction with the accompanying drawings, illustrate by way of example the principles of the invention.

BRIEF DESCRIPTION OF THE DRAWINGS

FIG. 1 is an elevational view, partially in section, depicting a stent embodying features of the invention and which is mounted on a balloon dilatation catheter and disposed within an artery.

FIG. 2 is an elevational view, partially in section, similar to that shown in FIG. 1 depicting the stent expanded within the artery, so that the stent embeds within the arterial wall.

FIG. 3 is an elevational view, partially in section, showing the expanded stent implanted in the artery wall after withdrawal of the balloon catheter.

FIG. 4 is a perspective view of a stent embodying features of the invention, shown in an unexpanded state.

FIG. 5 is a perspective view of a scent embodying features of the invention shown, in an unexpanded state.

DETAILED DESCRIPTION OF THE PREFERRED EMBODIMENTS

Figure 6:
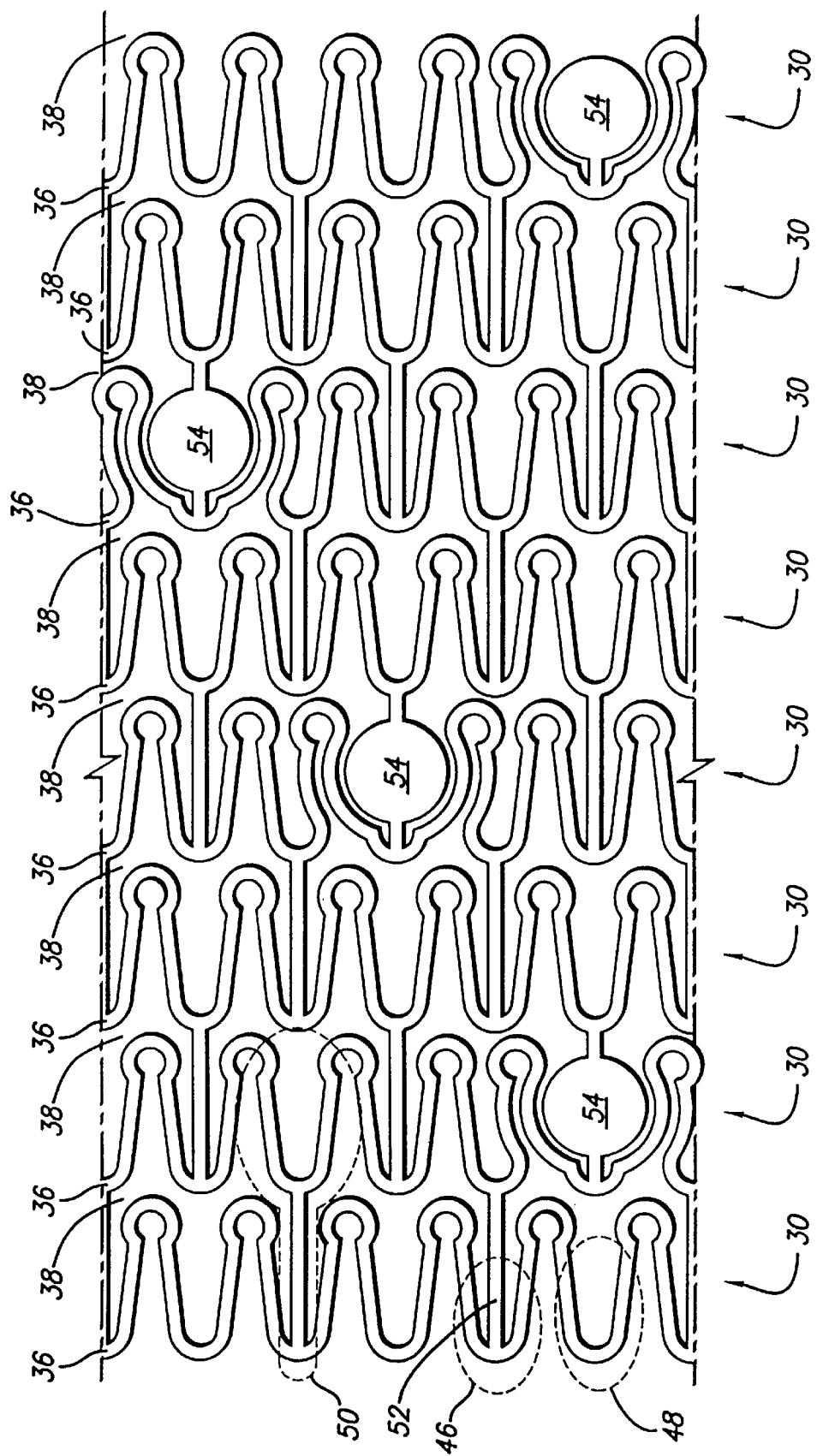
FIG. 6 is a plan view of a flattened section of the stent of the invention illustrating the pattern of the stent shown in FIG. 4.

The present invention stent improves on existing stents by providing a stent having a uniquely designed pattern with novel high-mass metal density that is readily visible under fluoroscopy. In one embodiment, the high-mass connecting links included in the stent's pattern provide for good radiopacity when used with conventional materials such as stainless steel and nitinol. Therefore, a stent in accordance with the present invention may be produced from a single conventional material and yet be readily visualized using well known fluoroscopy procedures without the aid of additional radiopaque markers or coatings. In addition to being fluoroscopically visible, the stent of the present invention also provides for good radial rigidity and longitudinal flexibility, as well as a high degree of scaffolding of a vessel lumen. The design of the high-mass connecting links and their spiral placement around the stent allow the stent to be visualized under fluoroscopy without regard to the stents orientation within a vessel lumen.

Referring now to FIG. 1, a stent 10 of the present invention is shown mounted on a catheter 12 having a lumen 14 and an inflation member 16. The stent and catheter are shown inside a lumen 24 of an arterial vessel 22. The stent is shown positioned across a small amount of arterial plaque 23 adhering to the lumen of the artery. The plaque is the remainder of an arterial lesion which has been previously dilated or radially compressed against the walls of the artery or has been partially removed from the artery. Lesion dilation is typically accomplished by an angioplasty procedure, while lesion removal is typically accomplished by an atherectomy procedure. These and other procedures for the treatment of arterial lesions are well known to those skilled in the art.

With most lesion treatment procedures, the treated artery suffers a degree of trauma and in a certain percentage of cases may abruptly collapse or may slowly narrow over a period of time which is referred to as restenosis. To prevent either of these conditions, the treated artery is often fitted with a prosthetic device, such as the stent 10 of the present invention. The stent provides radial support for the treated vessel and thereby prevents collapse of the lumen 24 and further provides scaffolding to prevent plaque prolapse within the lumen. The stent may also be used to repair an arterial dissection, or an intimal flap, both of which are commonly found in the coronary arteries, peripheral arteries and other vessels. In order to perform its function, the stent must be accurately placed across the lesion site. Therefore, it is critical that the stent be sufficiently radiopaque so that the operating surgeon can visually locate the stent under fluoroscopy during the implantation procedure. However, it is equally important that the stent not be too radiopaque. If the stent is overly radiopaque, i.e., too bright, the lumen and tissue surrounding the stent are likely to be obscured. Thus, the surgeon's view of the diseased tissue may be compromised leading to inaccurate stent placement.

With continued reference to FIG. 1, in a typical stent placement procedure, a guiding catheter (not shown) is percutaneously introduced into the cardiovascular system of a patient through the femoral arteries by means of a conventional Seldinger technique and advanced within a patient's vascular system until the distal end of the guiding catheter is positioned at a point proximal to the lesion site. A guide wire 20 and the stent-delivery catheter 12, are enclosed within a delivery sheath 26 (for use with self-expanding stents), and are introduced through the guiding catheter with the guide wire sliding within the stent-delivery catheter. The guide wire is first advanced out of the guiding catheter into the arterial vessel 22 and is directed across the arterial lesion. The stent-delivery catheter and protective sheath are subsequently advanced over the previously advanced guide wire until the stent is properly positioned across the lesion.

Referring now to FIG. 2, once in position, the delivery sheath 26 is retracted and the dilation balloon 16 is inflated to a predetermined size to radially expand the stent 10 against the inside of the artery wall and thereby implant the stent within the lumen 24 of the artery. The balloon is then deflated to a small profile so that the stentdelivery catheter may be withdrawn from the patient's vasculature and blood flow resumed through the artery.

Since the stent 10 is formed from an elongated tubular member, the rings and links of the stent are relatively flat in transverse cross-section, thus after implantation into the artery 22 as shown in FIG. 3, minimal interference with blood flow occurs. Eventually the stent becomes covered with endothelial cell growth which further minimizes blood flow interference. As should be appreciated by those skilled in the art, while the above-described procedure is typical, it is not the only method used in placing stents.

Typically, the stent 10 is laser cut from a solid tube. Thus, the stent does not possess discreet individual components. However, for the purposes of description it is beneficial to refer to the stent as being composed of cylindrical rings and connecting links. It is also beneficial to refer to the individual rings as being composed of a combination of U, W, and Y shaped elements, as will be described below.

Referring now to FIGS. 4 and 5, the stent 10 is made up of a plurality of cylindrical rings 30 which extend circumferentially around the stent. The stent has an initial delivery diameter 34 as shown in FIG. 5, and an expanded or implanted diameter 32 as shown in FIG. 4. Each cylindrical ring 30 has a cylindrical ring proximal end 36 and a cylindrical ring distal end 38 (see also FIG. 6). Each cylindrical ring 30 defines a cylindrical plane 40 which is a plane defined by the proximal and distal ends of the ring, 36 and 38, and the circumferential extent as the cylindrical ring travels around the cylinder. Each cylindrical ring includes a cylindrical outer wall surface 42 which defines the outermost surface of the stent, and a cylindrical inner wall surface 44 which defines the innermost surface of the stent. The cylindrical plane 40 follows the cylindrical outer wall surface.

Referring now to FIG. 6, for the purpose of illustration only, the stent 10 is shown as a flat pattern so that the pattern of rings and links may be more clearly viewed. Each ring may be visualized as being formed from a plurality of W-shaped elements 46, U-shaped elements 48, and Y-shaped elements 50. Interconnecting each cylindrical ring are one or more standard connecting links 52 or high-mass connecting links 54. Typically, each adjacent ring will be connected by a combination of standard and high-mass connecting links. In one exemplary embodiment, each ring is connected to each adjacent ring by three connecting links which are equally spaced at 120 degree intervals around the circumference of the stent. In the exemplary embodiment, one link of each set of links connecting every other adjacent ring is a high-mass link. In addition, each high-mass link is circumferentially offset from the preceding and succeeding high-mass link. Typically, the offset will match the link spacing, or 120 degrees in the exemplary embodiment. By circumferentially offsetting each high-mass link from each preceding high-mass link, a spiral pattern of high-mass links is formed around the body of the stent. This radial pattern allows the stent to be viewed under fluoroscopy regardless of the stent orientation during the implantation procedure.

Due to the present difficulties involved in machining variable thickness stents, in the exemplary embodiment, all of the members forming the links 52 and 54 and rings 30 of the stent 10 are of uniform thickness. Thus, in order to form the high-mass link, the shape chosen should have a comparatively large surface area. One such shape is that of a circular disk as is used in the exemplary embodiment shown in FIG. 4. However, any shape which provides for increased surface area over that of the standard link is suitable for use in forming high-mass links in accordance with the present invention. Suitable shapes are circles, rectangles, squares, triangles and trapezoids. Additionally, complex or nondescript geometric patterns, such as the high-mass connecting links 54 shown in FIGS. 12–15, whose shapes are not readily-identifiable geometric patterns, may be used. Although, in the exemplary embodiment the rings and links of the stent are of uniform thickness, this is not meant to be limiting. The high-mass links may be of either greater or lesser thickness than the other members which form the stent. What is important is that the high-mass links be of comparatively greater surface area than the standard links.

Figure 7:
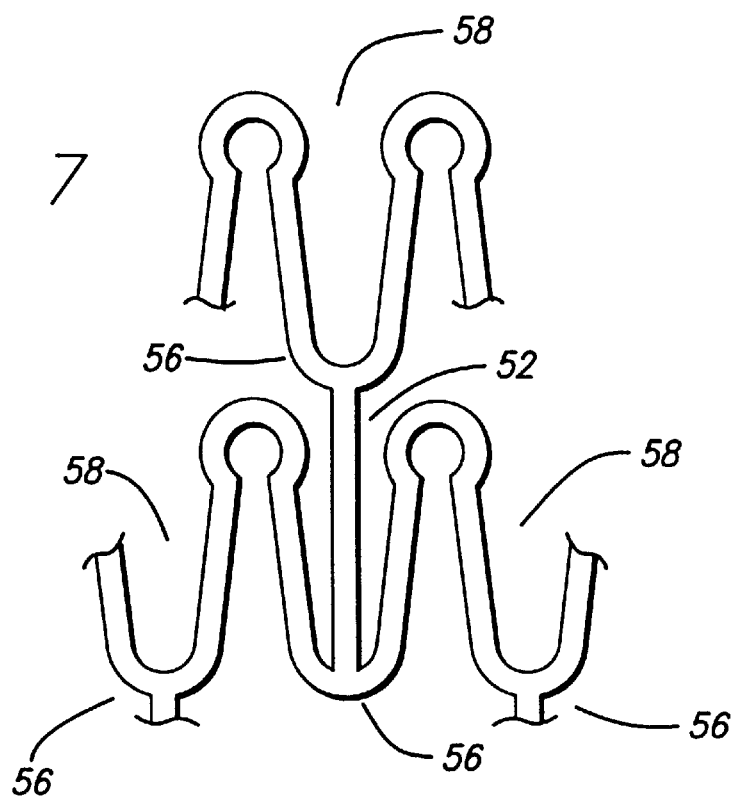
FIG. 7 is an enlarged sectional view of FIG. 4 depicting a Y-shaped portion of the cylindrical ring, where the Y-shaped portion includes a standard connecting link.
Figure 8:
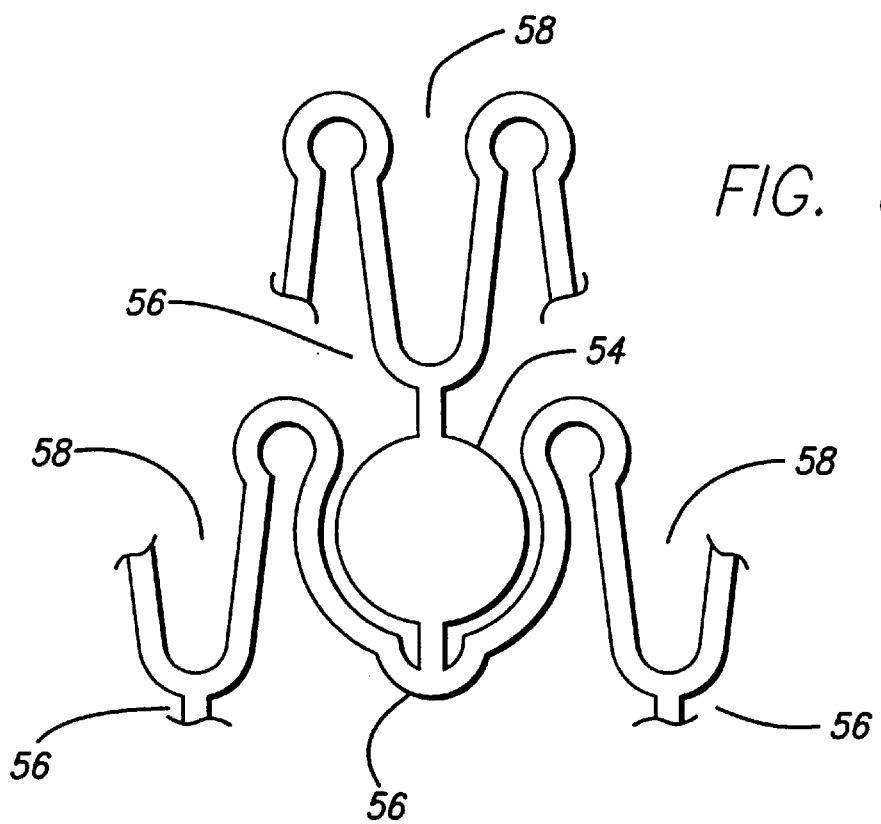
FIG. 8 is an enlarged sectional view of FIG. 4 depicting a Y-shaped portion of the cylindrical ring, where the Y-shaped portion includes a high-mass link.

FIG. 7 illustrates the standard connecting link 52 which has a surface profile in the form of a long, narrow rectangle of minimal surface area. FIG. 8 by contrast, illustrates the high-mass connecting link 54 which has a surface profile in the form of a circular disk and has approximately two to four times the surface area of the standard link and, in the exemplary embodiment, where both links are of the same thickness has approximately two to four times the mass of the standard link. In alternative embodiments where the links may be of different thicknesses, the high-mass link may have more or less mass than the standard link for a given surface area depending on the ratio of the thicknesses of the links.

Referring again to FIGS. 7 and 8, the U, W, and Y shaped elements of the cylindrical rings 30 have a plurality of peaks 56 and valleys 58. Each adjacent ring 30 is circumferentially offset from each subsequent ring such that the peaks of one ring are axially aligned with the valleys of the next adjacent ring. The connecting links 52 and 54 are positioned such that each link is within the valley of a U-shaped ring- element 48 and connects the element to a peak of an adjacent ring. FIG. 7 illustrates the connection with the standard link and FIG. 8 illustrates the connection with the high-mass link.

Figure 9:
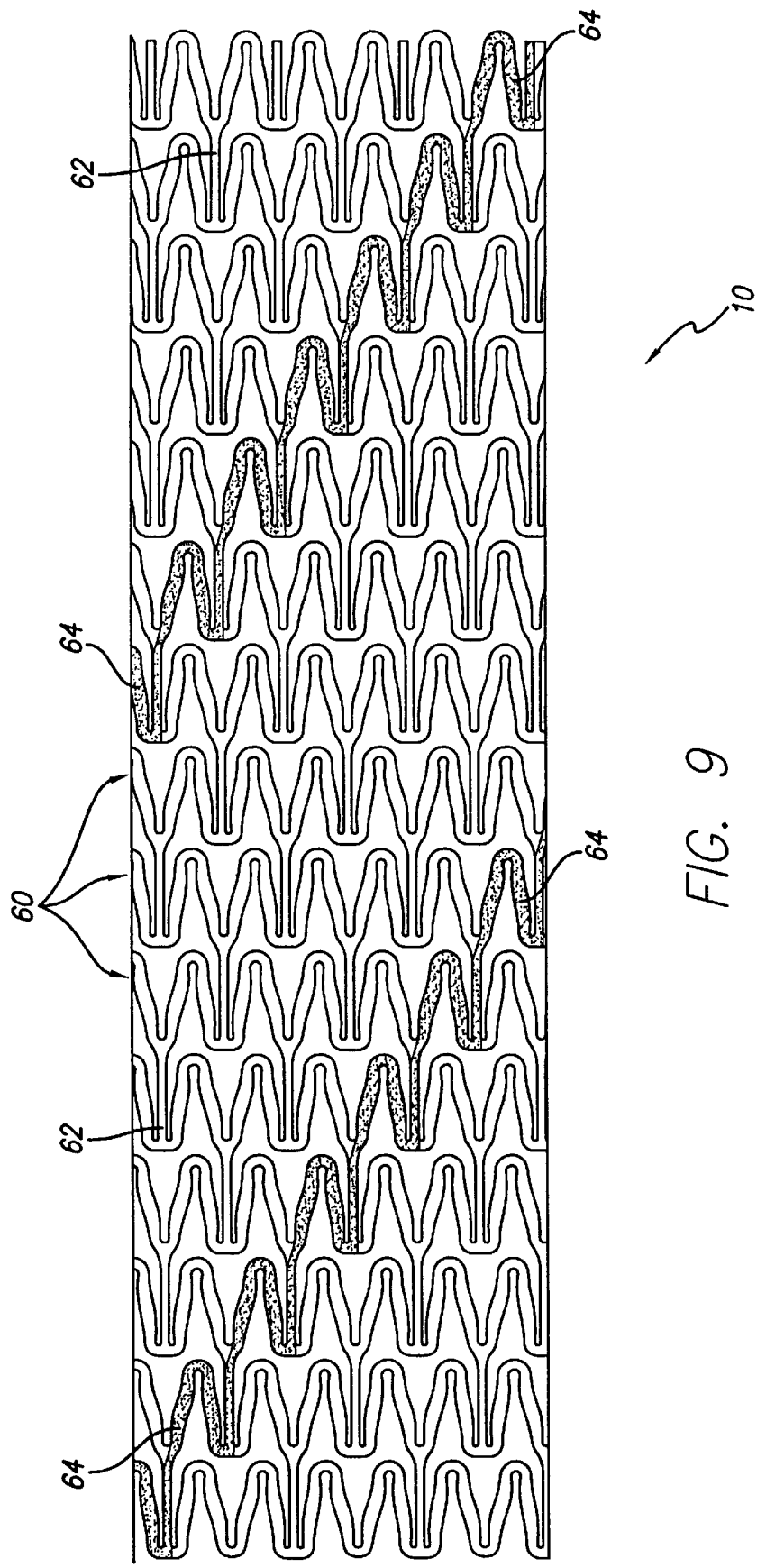
FIG. 9 is a plan view of a flattened section of the stent of the invention illustrating a portion of the stent having a high-mass metal density.
Figure 10:
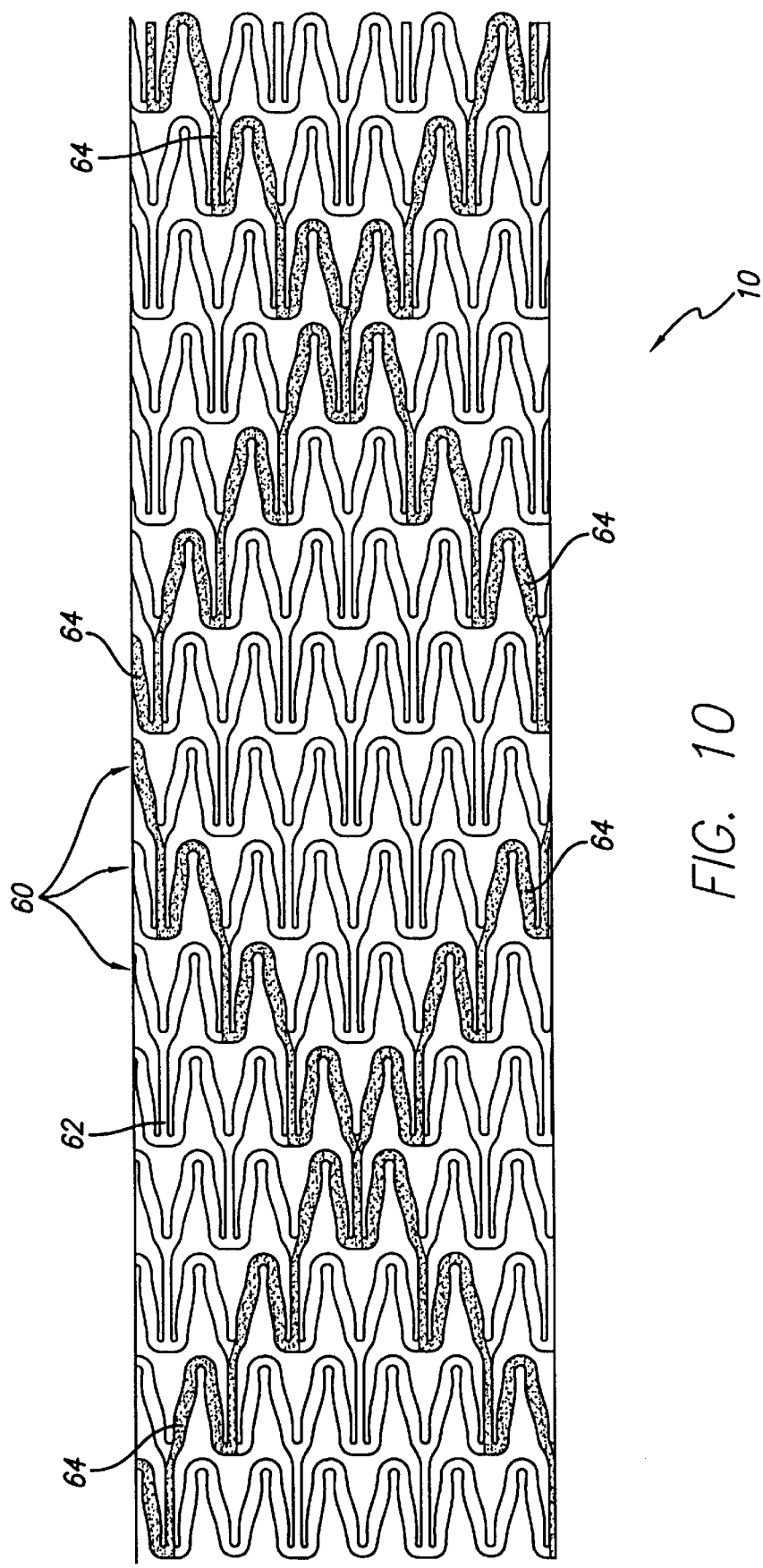
FIG. 10 is a plan view of a flattened section of the stent of the invention illustrating a portion of the stent having a high metal mass density.
Figure 11:
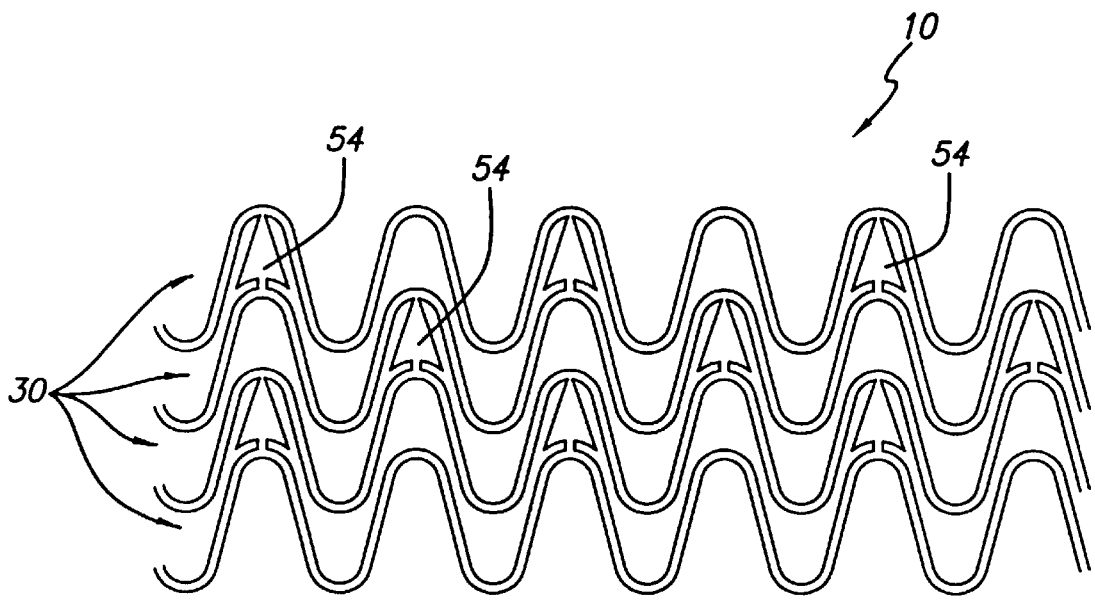
FIGS. 11–15 are plan views of a portion of a flattened section of the stent of the present invention showing alternative embodiments of links having a high-mass.
Figure 12:
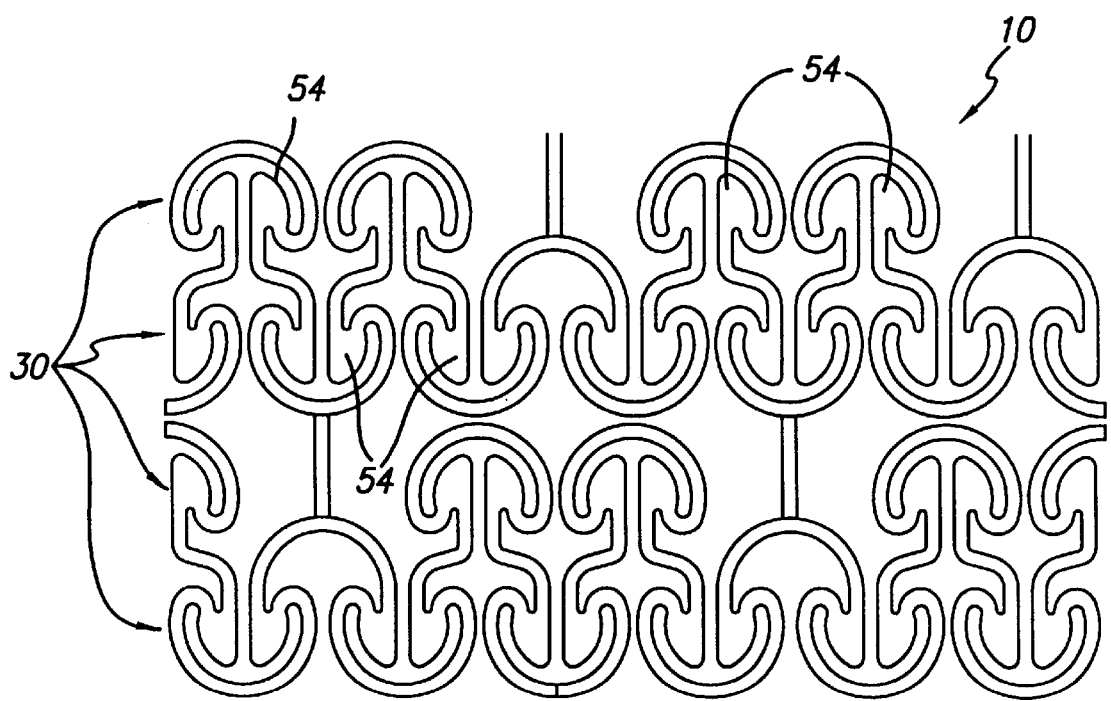
Figure 13:
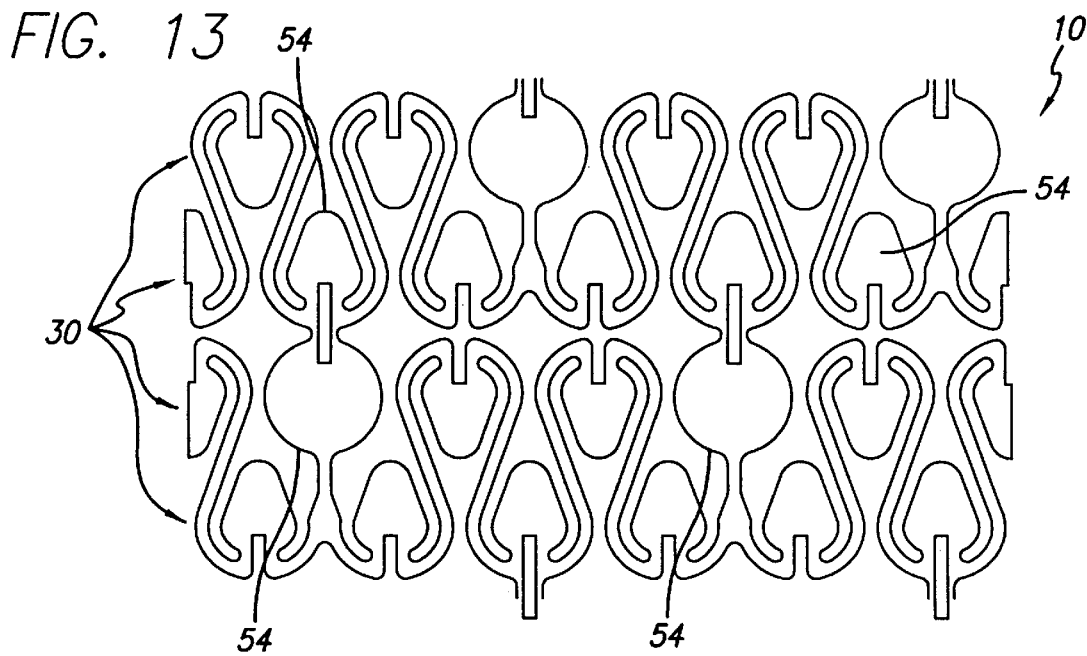
Figure 14:
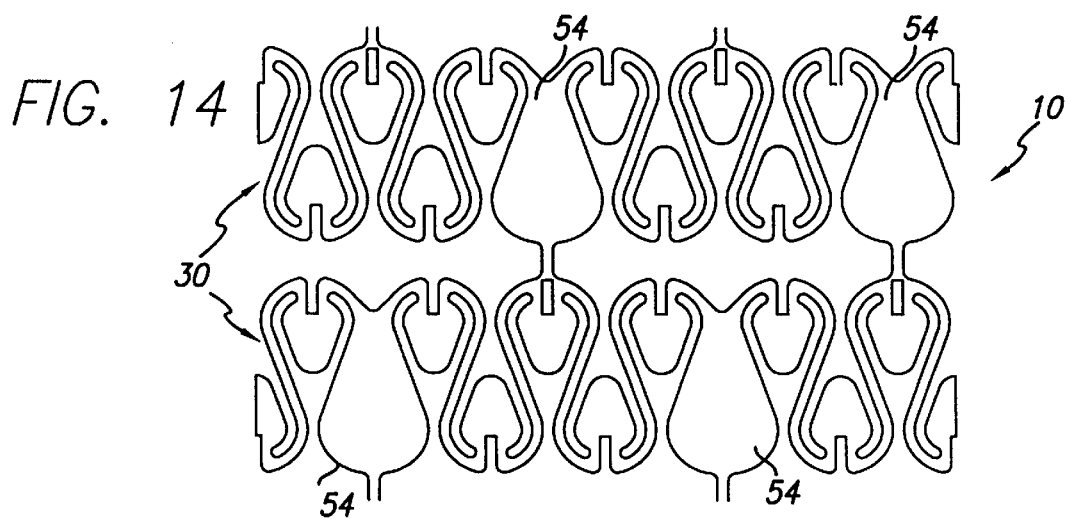
Figure 15:
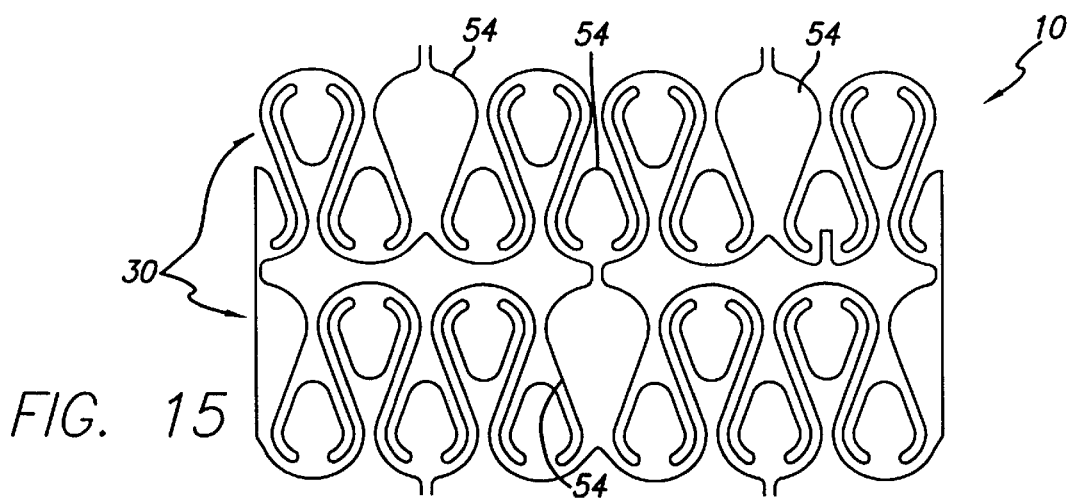

In another embodiment of the invention, as shown in FIGS. 9 and 10, stent 10 is comprised of a plurality of cylindrical rings 60 similar to those previously described. The stent is shown in its flattened condition for ease of illustration, however, it is in a cylindrical form for use in a body lumen. The cylindrical rings 60 are attached by link 62 in the manner previously described. In this embodiment, the high mass metal density is incorporated into the portion 64 of the rings that is illustrated by the darkened material in FIGS. 9 and 10. As shown in FIG. 9, the high mass portion 64 is in the form of a spiral when the stent is in a cylindrical configuration. Similarly, the high mass portion 64 shown in FIG. 10 is in a pattern that is easily detected under fluoroscopy and can help the physician determine the orientation of the stent more easily.

Alternative embodiments of the present invention stent are shown in FIGS. 11–15. The stent 10 has a number of cylindrical rings 30 that are connected by highmass links 54. The links are highly visible under fluoroscopy as previously described, for example, with reference to FIG. 6.

The stent 10 may be produced by several methods including electrodischarge machining and chemical etching. However, the preferred method is to laser cut a thin-walled tubular member, such as a hypotube. In this procedure, a computer controlled laser cuts away portions of the hypotube following a pre-programmed template to form the desired strut pattern. Methods and equipment for laser machining small diameter tubing may be found in U.S. Pat. Nos. 5,759,192 (Saunders) and U.S. Pat. No. 5,780,807 (Saunders), which have been assigned to Advanced Cardiovascular Systems, Inc.

The laser machining process leaves a thin heat effected zone around the pattern cut in the drawn tube and a resulting surface finish that is somewhat coarse and unsuitable for implantation in living tissue. The surface roughness of stents in the "as machined" condition is on the order of about 50–100 microns, while stents suitable for implantation within a blood vessel typically require a surface roughness of about 0.2 to 0.05 microns.

To achieve the required surface finish, stents are typically descaled and electro-polished. One method of descaling involves immersing the stents in an alkaline cleaner and ultrasonically agitating the stents for a selected period of time. Another method involves bead blasting stents with fine glass beads. There are other procedures for descaling that are well known to those skilled in the art.

The principles of electro-polishing are also known in the art. Typically, an item to be electro-polished is immersed in an electrolyte which comprises an aqueous acidic solution. The item to be polished is made a positive electrode (anode) and a negative electrode (cathode) is placed in close proximity to the anode. The anode and cathode are connected to a source of electric potential difference with the electrolyte completing the circuit between anode and cathode. Upon the passage of electric current through the electrolyte, metal is dissolved from the anode surface with protrusions being dissolved faster than depressions, thereby producing a smooth surface. The rate of material removal in an electro-polishing process is primarily a function of the electrolyte chosen and the current density in the electrolyte fluid.

Typically, with stainless steel stents, a final step in the electro-polishing process involves passivation of the newly polished surface. After removal from the electrolyte solution and rinsing with water, residual anions of the acid used in the electrolyte remain in contact with the polished surface. The presence of such surface anions leads to deterioration of the newly polished surface when the residual anions come into contact with calcium and magnesium ions which are commonly found in nondeionized water (ordinary tap water). To prevent surface deterioration, newly polished stents are immersed in a passivation bath which typically consists of a solution of nitric acid, deionized water, and sodium dichromate. The passivation bath neutralizes the residual anions and leaves a protective, corrosion resistant, strongly adherent, transparent, chromium dioxide coating on the newly polished surface.

With nickel-titanium alloy stents, however, the passivation step is generally not required. Nickel-titanium alloys tend to form a titanium oxide rich surface layer during initial heat treatment of the alloy which renders the alloy relatively impervious to the corrosive effects of any residual anions that may be left on the stent surface after electro-polishing.

The tubing used to make the strut assembly may be made of any biocompatible steel or shape memory alloy. The 300 series stainless steel alloys are well suited to this application with type 316L stainless steel per ASTM F138-92 or ASTM F139-92 grade 2 being preferred. Of the shape memory or super-elastic alloys, Nitinol, a 55% nickel –45% titanium alloy is preferred. Other shape memory alloys such as Ni—Ti—X (X being V, Co, Cu, Fe) ternary alloys, Cu—Al—Ni ternary alloys and Cu—Zn—Al ternary alloys are also suitable.

Typically, suitably sized tubing for making the stent 10 will have an outside diameter of about 0.020–0.095 inches, with a wall thickness of about 0.003–0.007 inches. However, tubing size will vary depending upon the application. It is preferred that the stent be machined from seamless tubing. However, tubing formed by rolling flat, sheet stock into a cylinder with welded longitudinal edges is also suitable, as is rolled sheet stock which has been drawn through a circular die.

It will be appreciated that a new stent having a pattern that allows the stent to be formed from a single material, such as stainless steel or Nitinol, and yet be sufficiently radiopaque to be readily visualized using fluoroscopy procedures without the need for an additional radiopaque coating has been presented. The stent achieves this ability by selectively locating high-mass connecting links about the circumference of the stent such that the stent may be visualized under fluoroscopy regardless of the stent's orientation during placement. Further, the high-mass connecting links are characterized by geometric shapes which possess a comparatively large surface area.

While only the presently preferred embodiment has been described in detail, as will be apparent to those skilled in the art, modifications and improvements may be made to the device and method disclosed herein without departing from the scope of the invention. Accordingly, it is not intended that the invention be limited, except as by the appended claims.

What is claimed:

1. A radiopaque intravascular stent for use in a body lumen, comprising:
   a plurality of cylindrical rings interconnected to form the stent, each cylindrical ring having a first delivery diameter and a second expanded diameter;
   each cylindrical ring having a proximal end and a distal end and a cylindrical wall extending circumferentially between the proximal end and the distal end of the cylindrical ring; and
   at least one connecting link attaching each cylindrical ring to an adjacent cylindrical ring, wherein at least one of the connecting links is a high-mass connecting link having a non-linear shape;
   wherein the stent is a unitary structure formed from a single material.

2. The stent of claim 1, wherein the high-mass connecting links have a configuration selected from the group consisting of circles, squares, rectangles, trapezoids, or triangles.

3. The stent of claim 1, wherein at least one high-mass connecting link attaches every other cylindrical ring to an adjacent cylindrical ring.

4. The stent of claim 3, wherein each high-mass connecting link is circumferentially offset from the preceding high-mass connecting link.

5. The stent of claim 4, wherein the circumferentially offset connecting links form a spiral pattern along the length of the stent.

6. The stent of claim 1, wherein each cylindrical ring comprises a plurality of peaks and valleys.

7. The stent of claim 6, wherein the peaks of each cylindrical ring are axially aligned with the valleys of each adjacent cylindrical ring.

8. The stent of claim 1, wherein the stent is formed from a tube.

9. The stent of claim 1, wherein the stent is formed from a metal alloy.

10. The stent of claim 1, wherein the stent is formed from stainless steel.

11. The stent of claim 1, wherein the stent is formed from a shape memory alloy.

12. A radiopaque stent for use in a body lumen, comprising:
    a plurality of cylindrical rings interconnected to form the stent, each cylindrical ring having a first delivery diameter and a second expanded diameter;
    each cylindrical ring having a plurality of peaks and valleys, the valleys of one cylindrical ring being circumferentially offset from the valleys of an adjacent cylindrical ring; and
    at least one connecting link attaching each cylindrical ring to an adjacent cylindrical ring, the connecting link being positioned substantially within one of the valleys and attaching the valley to an adjacent peak, wherein at least one of the connecting links is a high-mass connecting link having a non-linear shape;
    wherein the stent is a unitary structure formed from a single material.

13. The stent of claim 12, wherein the high-mass connecting links have a configuration selected from the group consisting of circles, squares, rectangles, trapezoids, or triangles.

14. The stent of claim 12, wherein at least one high-mass connecting link attaches every other cylindrical ring to an adjacent cylindrical ring.

15. The stent of claim 14, wherein each high-mass connecting link is circumferentially offset from the preceding high-mass connecting link.

16. The stent of claim 15, wherein the circumferentially offset connecting links form a spiral pattern along the length of the stent.

17. The stent of claim 12, wherein the stent is formed from a tube.

18. The stent of claim 12, wherein the stent is formed from a metal alloy.

19. The stent of claim 12, wherein the stent is formed from stainless steel.

20. The stent of claim 12, wherein the stent is formed from a shape memory alloy.

21. A radiopaque stent for use in a body lumen, comprising:
    a plurality of cylindrical rings interconnected to form the stent, each cylindrical ring having a first delivery diameter and a second expanded diameter, wherein each cylindrical ring has a proximal end and a distal end and a cylindrical wall extending circumferentially between the proximal end and the distal end, and further wherein the cylindrical rings are formed of a plurality of U-shaped portions, Y-shaped portions, and W-shaped portions; and
    at least one connecting link attaches each cylindrical ring to an adjacent cylindrical ring, the connecting links being positioned substantially within the cylindricial walls of the cylindrical rings and, wherein at least one of the connecting links is a high-mass link having a non-linear shape;

wherein the stent is a unitary structure formed from a single material.

22. The sent of claim 21, wherein the Y-shaped portions are formed from the combination of the U-shaped portions with the connecting links.

23. The stent of claim 21, wherein the W-shaped portions incorporate at least a portion of connecting links.

24. The stent of claim 21, wherein the high-mass connecting links have a configuration selected from the group consisting of circles, squares; rectangles, trapezoids, or triangles.

25. The stent of claim 21, wherein at least one high-mass connecting link attaches every other cylindrical ring to an adjacent cylindrical ring.

26. The stent of claim 25, wherein each high-mass connecting link is circumferentially offset from the preceding high-mass connecting link.

27. The stent of claim 26, wherein the circumferenitally offset connecting links form a spiral pattern along the length of the stent.

28. The stent of claim 21, wherein the stent is formed from a tube.

29. The stent of claim 21, wherein the stent is formed from a metal alloy.

30. The stent of claim 21, wherein the stent is formed from stainless steel.

31. The stent of claim 21, wherein the stent is formed from a shape memory alloy.

32. A radiopaque intravascular stent for use in a body lumen, comprising:

a plurality of cylindrical rings interconnected to form the stent, each cylindrical ring having a first delivery diameter and a second expanded diameter;

each cylindrical ring having a proximal end and a distal end and a cylindrical wall extending circumferentially between the proximal end and the distal end of the cylindrical ring; and at least a portion of each ring having a higher mass than the rest of the ring, and wherein the portion of adjacent rings having a higher mass are circumferentially offset such that a pattern of higher mass metal is defined, the pattern extending from the proximal end of the stent to the distal end of the stent;

wherein the stent is a unitary structure formed from a single material.

33. The stent of claim 32, wherein the pattern defined is geometric.

34. The stent of claim 33, wherein the geometric pattern is helical.

35. The stent of claim 32, wherein the portion of each ring having higher mass includes at least one connecting link.

* * * * *

UNITED STATES PATENT AND TRADEMARK OFFICE
CERTIFICATE OF CORRECTION

PATENT NO.    : 6,652,579 B1
DATED         : November 25, 2003
INVENTOR(S)   : Cox et al.

It is certified that error appears in the above-identified patent and that said Letters Patent is hereby corrected as shown below:

<u>Title page,</u>
Item [56], References Cited, OTHER PUBLICATIONS, "Union Carbide," 14<sup>th</sup> reference, should read as follows:
-- Union Carbide, Electronic Materials, Parylene Products, Oct. 1977, No. 2 Revision 1 (9 pages). --
"Hahn, Allen W., et al." 7<sup>th</sup> reference, should read as follows:
-- Hahn, Allen W., et al., Glow Discharge Polymers as Coatings for Implanted Devices, ISA, pp. 109-113, 1981. --
"Maass, et al.," 12<sup>th</sup> reference, should read as follows:
-- Maass, et al., Radiological Follow-Up of Transluminally Inserted Vascular Endoprostheses: An Experimental Study Using Expanding Spirals, Radiology Journal, pp. 659-663, 1984. --

<u>Column 4,</u>
Line 52, delete "unexpanded" and insert -- expanded --.
Line 53, delete "scent" and insert -- stent --.

<u>Column 6,</u>
Line 20, delete "stentdelivery" and insert -- stent-delivery--.

<u>Column 8,</u>
Line 6, delete "highmass" and insert -- high-mass --.

Signed and Sealed this

Fourth Day of May, 2004

JON W. DUDAS
*Acting Director of the United States Patent and Trademark Office*